United States Patent [19]

Mann et al.

[11] Patent Number: 5,049,491
[45] Date of Patent: Sep. 17, 1991

[54] IMMUNOLOGIC DETECTION OF FACTOR V(VA) FRAGMENTS IN HEMORRHAGIC AND THROMBOTIC CLINICAL SETTINGS

[75] Inventors: Kenneth G. Mann, Shelbourne; Paula B. Tracy, Essex Junction, both of Vt.

[73] Assignee: The University of Vermont, Burlington, Vt.

[21] Appl. No.: 122,985

[22] Filed: Nov. 19, 1987

[51] Int. Cl.$^5$ .................... C12Q 1/00; C07K 15/06; G01N 33/53
[52] U.S. Cl. .................... 435/7.92; 422/61; 436/548; 530/381
[58] Field of Search .............. 435/7; 436/548; 422/58, 422/61; 530/381

[56] References Cited

PUBLICATIONS

Ratnoff, "Thrombosis and the hypercoagulable state", Embase No. 85002264, dialog acc. no. 5756754, 1984.

Primary Examiner—Robert J. Warden
Assistant Examiner—Jill Johnston
Attorney, Agent, or Firm—David G. Conlin; Ernest V. Linek; George W. Neuner

[57] ABSTRACT

The present invention is directed to immunochemical detection procedures, e.g., using both Western blotting and direct immunoassays, for Factor V/Va and Factor V/Va fragments, which can thus be used; (a) in a predictive manner to evaluate the existence and/or extent of a thrombotic complication; (b) to monitor the efficacy of prophylaxis for a thrombotic condition; and (c) as a means to evaluate potential risk of hemorrhage during thrombolytic therapy.

19 Claims, 1 Drawing Sheet

AMINO ACID SEQUENCE OF FIRST TEN RESIDUES

1. AQLRQFYVAA
2. SQHLDNFSNQ
3. GIQRAADIEQ
4. SFRNSSLNQE
5. TFHPLRSEAY
6. SNNGNRRNYY
7. LTSSEMKKSH

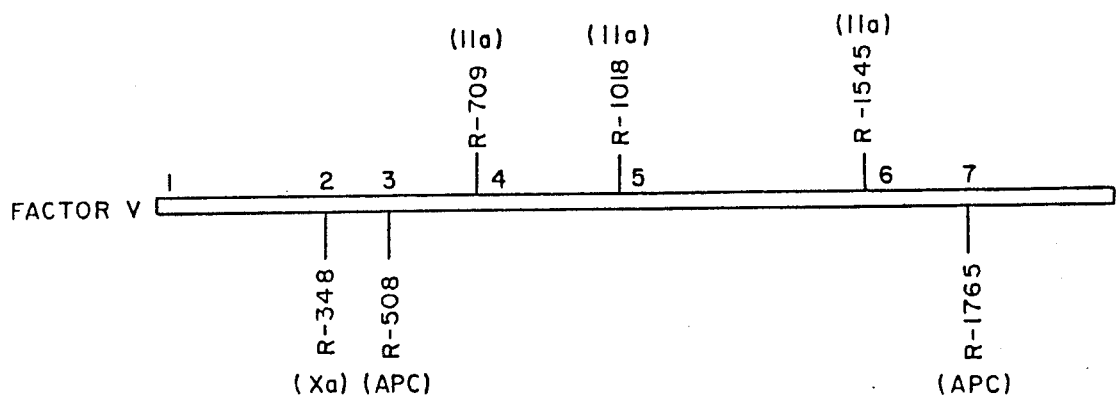
AMINO ACID SEQUENCE OF FIRST TEN RESIDUES
1. AQLRQFYVAA
2. SQHLDNFSNQ
3. GIQRAADIEQ
4. SFRNSSLNQE
5. TFHPLRSEAY
6. SNNGNRRNYY
7. LTSSEMKKSH

IMMUNOLOGIC DETECTION OF FACTOR V(VA) FRAGMENTS IN HEMORRHAGIC AND THROMBOTIC CLINICAL SETTINGS

BACKGROUND OF THE INVENTION

The Factor V molecule is an essential co-factor in the blood clotting mechanism. While the activity associated with Factor V was first identified (by virtue of its absence) in a bleeding patient in 1943, Dr. Mann's laboratory was the first to isolate bovine Factor V as a homogeneous protein, (Nesheim et al., *J. Biol. Chem.*, 254: 508–517 (1979)). Human Factor V was isolated subsequently (Katzmann et al., *Proc. Natl. Acad. Sci. USA*, 78: 162–166 (1981)). Dr. Mann's laboratory was the first to prepare both polyclonal (Tracy et al., *Blood*. 60: 59–63 (1982)) and monoclonal antibodies to this protein (Foster et al., *Blood*, 61: 1060–1067 (1983); Foster et al., *J. Biol. Chem.*, 258: 5608–5613 (1983); and Foster et al., *Thromb. Res*.28: 649–661 (1982)). In addition, his laboratory has identified the entire amino acid sequence of the molecule (Jenny et al., *Proc. Natl. Acad. Sci. USA*, 84: 4846–4850 (1987)) in addition to the sites at which it is cleaved by various plasma proteases. (See for example, Jenny et al., supra and Odegaard et al., *J. Biol. Chem.*, 262: 11233–11238 (1987)). Dr. Mann and his coworkers have conducted extensive studies of how Factor V functions and have identified the following features:

A. The protein circulates as a pro-cofactor, which is not functional in coagulation reactions, (Nesheim et al., *J. Biol. Chem.*, 254: 10952–10962 (1979)).

B. The pro-cofactor can be cleaved by thrombin or by Factor Xa (two blood clotting enzymes) to produce the active co-factor, Factor Va, see for example, Nesheim et al., *J. Biol. Chem.*, 254: 1326–1334 (1979); Tracy et al., *J. Biol. Chem.* 258: 662–669 (1983); Tracy et al., *Proc. Natl. Acad. Sci. USA*, 80: 2380–2384 (1983) and Foster et al., *J. Biol. Chem.*, 258: 1398–13977(1983).

C. Factor Va can be inactivated by cleavage by the anticoagulant enzyme activated protein C, (Tracy et al., *Boood*, supra and Canfield et al., *Am. Heart Assn.*, 51st Sci Session, Dallas, Tex., Nov. 13–16, 1978, Circulation 57–58: II, p. 210, Abst. #86, (1978)).

D. The fibrinolytic enzyme plasmin has two effects on Factor V. It can activate Factor V to Factor Va and then inactivate Factor Va. See for example, Omar et al., *J. Biol. Chem.*, 262: 9750–9755 (1987) and Lee et al., *Am. Soc. Hemat.*, 29th Ann. Mtg., Washington, D.C. Dec. 5–8, 1987, as published in *Blood*, 70: p389a, Abst. #1412 (1987).

It has previously been reported that several discrete Factor V and/or Factor Va peptides are produced by the proteolytic action of various enzymes which are activated during blood clotting or fibrinolytic reactions. These enzymes include thrombin, Factor Xa, activated protein C and plasmin. The peptides produced by the action of these proteases are distinguishable from one another based on their apparent molecular weight, amino acid composition and sequence.

The observation of these Factor V and/or Factor Va peptides in vivo was first accomplished by the infusion of radiolabeled Factor V into dogs and the subsequent identification of the Factor V and/or Va fragments present in plasma by gel electrophoresis and autoradiography. (See for example, Giles et al., *J. Clin. Invest.* 74: 2219–2225 (1984) and Nesheim et al., supra).

The separation of these Factor V and/or Factor Va peptides has now been accomplished by the present inventors, through the immunochemical detection of the fragments resulting from in vivo proteolysis of endogenous plasma Factor V in patients with disseminated intravascular coagulation (DIC) using Western blotting techniques and a polyclonal anti-human Factor V antibody. See, Rubin et al., *Am. Heart Assn.* 9th Sci. Session, Dallas, Tex., Nov. 19, 1986, Circulation 74: II, p. 411, Abst. #1639 (1986). Based upon studies conducted in animals and in humans, the present inventors have verified the detectability and correlation between the presence of these Factor V and Factor Va fragments and the extent (or presence) of coronary artery disease states including disseminated intravascular coagulation (DIC) and exercise induced angina pectoris.

SUMMARY OF THE INVENTION

As a consequence of the central position of Factor V in the blood clotting scheme, activation to Factor Va and the consequences of inactivation, Factor V provides the ideal marker to evaluate the existence of a thrombotic condition or the potential for hemorrhagic complication.

Thus, the present invention is directed to immunochemical detection procedures, e.g., using both Western blotting and direct immunoassays, for Factor V/Va and Factor V/Va fragments, which can thus be used; (a) in a predictive manner to evaluate the existence and/or extent of a thrombotic complication; (b) to monitor the efficacy of prophylaxis for a thrombotic condition; and (c) as a means to evaluate potential risk of hemorrhage during thrombolytic therapy.

In each of the above described conditions (i.e., thrombosis or hemorrhage) specific sets of Factor V fragments are produced and analytical methodology currently exists for their quantitative evaluation in blood samples.

Hence, the present invention is particularly directed to quantitative and qualitative assay techniques useful for determining the amount and/or presence of Factor V and/or Factor Va in mammalian blood and/or plasma samples, which can be used in the clinical diagnosis of thrombosis and hemorrhagic risk.

BRIEF DESCRIPTION OF THE FIGURE

The figure illustrates the six already identified cleavage sites of the human Factor V molecule, and the single letter codes for the N-terminal amino acid sequence at each of the identified sites. For a translation of the single letter amino acid codes see, A. L. Lehninger, "Biochemistry," 2nd ed., pp 77–75, Worth Publishers (1977).

DETAILED DESCRIPTION OF THE PREFERRED EMBODIMENTS

The present invention stems from the observation that through the use of either monoclonal or polyclonal antibodies, one can recognize specific Factor V and/or Factor Va peptides associated with either its activation or inactivation.

Factor V has a central position in the blood coagulation response and is very susceptible to proteolytic cleavage by several of the enzymes produced during this response. Consequently the proteolytic activation of Factor V to Factor Va and its subsequent additional proteolytic inactivation, make it an ideal marker to assess the existence of a thrombotic or hemorrhagic condition.

During either thrombotic or hemorrhagic events, specific Factor V and/or Factor Va fragments are produced which can be quantitated in patient plasma samples using direct immunological techniques. The quantitation of these peptides will allow for (1) the diagnosis and extent of either a thrombotic or hemorrhagic complication, and the evaluation of (2) the efficacy of treatment of a thrombotic condition or (3) the potential risk of hemorrhage following thrombolytic therapy.

The present inventors have successfully detected early intravascular coagulation as evidenced by the cleavage of Factor V in the plasma of patients experiencing ischemic changes associated with coronary artery disease.

Plasma of patients with symptoms of intravascular coagulation and fibrinolysis showed a different Factor V cleavage pattern, most likely attributable to plasmin activity. Similar peptide patterns have been observed in the plasma of patients undergoing fibrinolytic therapy.

Thus, the present invention is directed to methods for the clinical assessment of significant coagulable and potentially hemorrhagic states comprising the determination of the Factor V cleavage pattern.

Factor V and the Factor Va peptides can all be prepared by isolation of the naturally occurring product or by synthesis, e.g., by using automated peptide synthesis equipment, since the sequence of all the peptides are known. See, for example, Nesheim et al., *J. Biol Chem.*, 259: 3187-3196 (1983) and Jenny et al., *Proc. Natl. Acad. Sci. USA*, 84: 4846-4850 (1987). With the formation of monoclonal antibodies specific for Factor V and each of the Factor Va peptides, one may also isolate the naturally occurring peptides by use of immunoaffinity chromatography.

Antibodies to Factor V and/or Factor Va may be prepared in accordance with known methods for immunizing test animals, for example, by continuous subcutaneous or intramuscular injections of suitable quantities (e.q., from about 100 micrograms to about 0.1 mg) of Factor V and/or Factor Va in mixture with a suitable adjuvant (e.g., Freund's complete). The antibodies formed in the animal may then be recovered from the blood serum of the animal by well known techniques. One preferred polyclonal antibody is a burro anti-human Factor V polyclonal antibody which recognizes all of the Factor Va peptides in addition to the intact Factor V molecule. See, for example, Tracy et al., *Blood*, 60: 59-63 (1982).

Monoclonal antibodies to Factor V and Factor Va can be prepared using standard techniques for preparing such antibodies. For example, BALB/c mice are first immunized with an appropriate amount of Factor V or Factor Va. The spleen cells obtained from the immunized mice are then fused with an appropriate myeloma cell, e.q., NS-1 murine myeloma cells. Hybrid cell cultures are then assayed for the production of antibodies to Factor V or Factor Va. Cells from positive cultures are subcloned by limited dilution and grown in ascites tumors in BALB/c mice. See, for example, Foster et al., *Blood*, 61: 1060-1067 (1983); Foster et al., *J. Biol. Chem.*, 258: 5608-5613 (1983); and Foster et al., *Thromb. Res.*, 28: 649-661 (1982); Katzmann et al., *Proc. Natl. Acad. Sci. USA*, 78: 162-166 (1981)).

The preparation of monoclonal antibodies associated with specific cleavage sites in the intact molecules (see the Figure) is an especially preferred embodiment in the present invention, as such antibodies may not cross react with the intact molecule.

Currently, the proven method of detection is through the use of Western blotting techniques of electrophoretically separated Factor V peptides. Specific immunoassays for these peptides can be employed for the detection of these species, preferably using monoclonal antibodies specific for either Factor V or one of the Factor Va peptides.

Two especially preferred assay techniques for detection of these peptides are the so-called double antibody and solid phase enzyme-linked immunoassays methods. These assays preferably utilize monoclonal antibodies specific for the peptide(s) in question and thus allow for detection of these peptides even in the presence of the intact molecule. Since some of the peptides in question are only non-covalently associated through metal ion dependent interaction, they can be easily assayed of chelating agents which an dissociate the various fragments. See for example, Foster et al., *J. Biol. Chem.*, 258: 5608-5613 (1983). Thus, in the most preferred embodiments of the present invention, patient plasma is assayed directly.

By utilizing Western blots and the polyclonal burro anti-human Factor V antibody, the present inventors were able to detect early intravascular coagulation as evidenced by the activation of Factor V in DIC and ischemic changes associated with coronary artery disease.

This methodology allowed for the sensitive detection (40 nanograms) of Factor V activation in plasma samples obtained via indwelling catheterization or phlebotomy. In the majority of samples analyzed from DIC patients, there was a loss of single chain Factor V ($M_r=330K$ daltons) and a corresponding increase in both the 220K dalton activation intermediate and the 150K dalton activation peptide. Smaller peptide fragment (i.e., less than 150 daltons) were occasionally seen in some, but not all patients.

In catheter samples collected from patients experiencing exercise-induced angina, the methodology described above demonstrated the activation of Factor V to the 220K dalton intermediate and the 94K dalton Factor Va subunit. Simultaneously drawn peripheral blood samples showed no evidence of Factor V activation. Similarly, there was no evidence of Factor V activation in identically obtained plasma samples from stress tested patients without angina.

Thus, on the basis of these observations, the present inventors have established the correlation between Factor V activation and clinically significant coagulable states, and the clinical ability to monitor and assess these conditions.

By employing standard immunoassay techniques, the levels of Factor V and/or Factor Va may be quantitatively determined. The activated Factor V products are undetectable in normal serum, and its quantitation by Western blot and immunoassay techniques has proven useful as an indication of a thrombotic or hemorrhagic condition.

In general, single antibody immunoassays require the separation of a labeled antigen, e.g., Factor V and/or Factor Va, into bound and unbound fractions after its interaction with an antibody, e.g., anti-Factor V and/or anti-Factor Va, in the presence of an unknown quantity of unlabeled antigen from a test sample. The ratio of bound-to-free labeled antigen is related to the concentration of unknown antigen in the test sample by comparison to a curve demonstrating binding in the presence of standards of known concentration.

As described above, double antibody assays may also be employed herein. A double antibody reaction is especially useful when low or unknown primary antibody levels are encountered. For example, a primary antibody such as burro anti-human Factor V antibody may be employed to react with Factor V and/or Factor Va from blood plasma. Analysis of this reaction is then accomplished by for example, immunofluorescence by reacting a second antibody such as, fluorescein-conjugated goat anti-burro antibody, with a bound complex of primary antibody and Factor V and/or Factor Va.

This invention also encompasses a diagnostic kit for testing plasma samples for Factor V, Factor Va, and/or fragments thereof. The kit includes an ampoule or the like containing antibodies against Factor V, Factor Va, and/or fragments thereof, preferably in freeze-dried, i.e., lyophilized form, and also an ampoule containing a labeled form of Factor V, Factor Va, and/or fragments thereof, preferably in freeze-dried, i.e., lyophilized form. The kit optionally contains an ampoule of Factor V, Factor Va, and/or fragments thereof, in a predetermined concentration for use as a control.

The publications referred to herein, to the extent necessary, are hereby incorporated herein by reference.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A method of diagnosing thrombotic or hemorrhagic events in humans comprising monitoring human blood plasma for changes in the levels of the fragmentation pattern of Factor V or Factor Va.

2. The method of claim 1, wherein the thrombotic or hemorrhagic event is associated with disseminated intravascular coagulation.

3. The method of claim 2, wherein the change in plasma levels of the fragmentation pattern of Factor V being monitored is a decrease in the level of Factor V (330K daltons) and an increase in the levels of the 220K dalton activation intermediate and the 150K dalton activation peptide.

4. The method of claim 1, 2, or 3, wherein the monitoring is conducted using Western blotting techniques on electrophoretically separated Factor V peptides.

5. The method of claim 1, 2, or 3, wherein the monitoring is conducted using immunoassay techniques.

6. The method of claim 5, wherein the immunoassay is a double antibody, solid phase enzyme linked assay.

7. The method of claim 5, wherein the assay utilizes monoclonal antibodies specific to Factor V, Factor Va, or fragments thereof.

8. The method of claim 5, wherein the assay utilizes polyclonal antibodies to Factor V or Factor Va.

9. A method of evaluating the treatment of a thrombotic or hemorrhagic condition in humans in need of such treatment, comprising monitoring human blood plasma for changes in the levels of the fragmentation pattern of Factor V o Factor Va.

10. The method of claim 9, wherein the thrombotic or hemorrhagic event is associated with disseminated intravascular coagulation.

11. The method of claim 10, wherein the change in plasma levels of the fragmentation pattern of Factor V being monitored is a decrease in the level of Factor V (330K daltons) and an increase in the levels of the 220K dalton activation intermediate and the 150K dalton activation peptide.

12. The method of claim 9, wherein the thrombotic or hemorrhagic event is associated with exerciseinduced angina.

13. The method of claim 12, wherein the change in plasma levels of the fragmentation pattern of Factor V being monitored is represented by a decrease in the level of Factor V (330K daltons) and an increase in the levels of the 220K dalton activation intermediate and the 94K dalton Factor V subunit.

14. The method of claim 9, 10, 11, 12, or 13, wherein the monitoring is conducted using Western blotting techniques on electrophoretically separated Factor V peptides.

15. The method of claim 9, 10, 11, 12, or 13, wherein the monitoring is conducted using immunoassay techniques.

16. The method of claim 15, wherein the immunoassay is a double antibody, solid phase enzyme linked assay.

17. An assay kit for monitoring human blood plasma levels for Factor V, Factor Va, or fragments thereof comprising in combination:
    (a) an ampoule containing anti-human antibodies having epitope specificity for human Factor V, Factor Va, or fragments thereof; and
    (b) an ampoule containing a labeled form of Factor V, Factor Va, or fragments thereof.

18. The test kit of claim 17, wherein the antigen and antibodies are in lyophilized form.

19. The test kit of claim 17 or 18, further comprising an ampoule of Factor V and/or Factor Va, or fragments thereof, in a predetermined concentration for use as a control.

* * * * *

UNITED STATES PATENT AND TRADEMARK OFFICE
CERTIFICATE OF CORRECTION

PATENT NO. : 5,049,491  
APPLICATION NO. : 07/122985  
DATED : September 17, 1991  
INVENTOR(S) : Mann et al.

Page 1 of 1

It is certified that error appears in the above-identified patent and that said Letters Patent is hereby corrected as shown below:

Column 1, line 5.

Please insert the following text:

--STATEMENT OF GOVERNMENT SUPPORT

Funding for this invention was provided in part by the Government of the United States of America, through Grant No. HL034575, by the National Institutes of Health. The Government has certain rights in this invention.--

Signed and Sealed this

Eighteenth Day of July, 2006

JON W. DUDAS  
*Director of the United States Patent and Trademark Office*